US012678447B2

(12) United States Patent
Pasparakis et al.

(10) Patent No.: US 12,678,447 B2
(45) Date of Patent: Jul. 14, 2026

(54) COMBINATIONS OF RIPK₁- AND IKK-INHIBITORS FOR THE PREVENTION OR TREATMENT OF IMMUNE DISEASES

(71) Applicant: Universität zu Köln, Cologne (DE)

(72) Inventors: Manolis Pasparakis, Cologne (DE); Nikos Oikonomou, Cologne (DE); Apostolos Polykratis, Cologne (DE)

(73) Assignee: Universität zu Köln (DE)

( * ) Notice: Subject to any disclaimer, the term of this patent is extended or adjusted under 35 U.S.C. 154(b) by 162 days.

(21) Appl. No.: 16/769,972

(22) PCT Filed: Dec. 7, 2018

(86) PCT No.: PCT/EP2018/084055
§ 371 (c)(1),
(2) Date: Jun. 4, 2020

(87) PCT Pub. No.: WO2019/110832
PCT Pub. Date: Jun. 13, 2019

(65) Prior Publication Data
US 2020/0383995 A1 Dec. 10, 2020

(30) Foreign Application Priority Data
Dec. 7, 2017 (EP) .................................... 17205864

(51) Int. Cl.
A61K 31/553 (2006.01)
A61K 31/4178 (2006.01)
A61K 45/06 (2006.01)

(52) U.S. Cl.
CPC ........ A61K 31/553 (2013.01); A61K 31/4178 (2013.01); *A61K 45/06* (2013.01)

(58) Field of Classification Search
CPC .......................... A61K 31/4178; A61K 31/553
See application file for complete search history.

(56) References Cited

FOREIGN PATENT DOCUMENTS

| EP | 3 017 825 | 5/2016 | |
| EP | 3494994 A1 | 6/2019 | |
| WO | WO 2002/060386 | 8/2002 | |
| WO | WO2007146602 A8 | 10/2009 | |
| WO | WO-2016027253 A1 * | 2/2016 | ............. A61K 31/55 |

OTHER PUBLICATIONS

Gillooly et al (JPET, 2009; 331:349-360) (Year: 2009).*
Llona-Minguez et al (Pharm Pat Analyst, 2013; 2(4):481-498) (Year: 2013).*
Jie et al (Oncotarget, 2016; 7(15):19367-19381) (Year: 2016).*
Young E. IKKb as a therapeutic intervention point for diseases related to inflammation. In: Anti-Inflammatory Drug Discovery. RSC Publishing, London, UK, 255-296 (2012), pp. 255 and 280). (Year: 2012).*

International Preliminary Report on Patentability for PCT/EP2018/084055, issued Jun. 9, 2020, 8 pages.
Written Opinion in EP 17205864.6, dated Sep. 11, 2018, 6 pages.
Liao, ed., Pediatric Hematology, Najjin Science and Technology, Apr. 2005. Third Chapter 17, Section 2 Neutrophilia, pp. 278-279 (English translation included).
Alcamo et al., "Targeted Mutation of TNF Receptor I Rescues the RelA-Deficient Mouse and Reveals a Critical Role for NF-κB in Leukocyte Recruitment," J Immunol (2001) 167(3):1592-1600.
Bohrer et al., "Role of NFkappaB in the mortality of sepsis," J Clin Inv (1997) 100(5):972-985.
Brand et al., "Activated transcription factor nuclear factor-kappa B is present in the atherosclerotic lesion," J Clin Invest (1996) 97(7):1715-1722.
Dondelinger et al., "NF-kB-Independent Role of IKKa/IKKβ in Preventing RIPK1 Kinase-Dependent Apoptotic and Necroptotic-Cell Death during TNF Signaling," Mol Cell (2015) 60(1):63-76.
Greten et al., "NF-κB Is a Negative Regulator of IL-1β Secretion as Revealed by Genetic and Pharmacological Inhibition of IKKβ," Cell (2007) 130(5):P918-931.
International Search Report for PCT/EP2018/084055, dated Mar. 14, 2019, 17 pages.
Liu et al., "Necrostatin-1 reduces intestinal inflammation andcolitis-associated tumorigenesis in mice," Am J Cancer Res (2015) 5(10):3174-3185.
Luedde et al., "Deletion of NEMO/IKKγ in Liver Parenchymal Cells Causes Steatohepatitis and Hepatocellular Carcinoma," Cancer Cell (2007) 11(2):119-132.
Nenci et al., "Epithelial NEMO Links Innate Immunity to Chronic Intestinal Inflammation," Nature (2007) 446 (7135):557-561.
Pasparakis et al., "TNF-mediated Inflammatory Skin Disease in Mice With Epidermis-Specific Deletion of IKK2," Nature (2002) 417(6891):861-866.
Polykratis et al., "Cutting Edge: RIPK1 Kinase Inactive Mice are Viable and Protected from TNF-Induced Necroptosis In Vivo," J Immunol (2014) 193(4):1539-1543.
Strnad et al., "IkB kinase inhibitors for treating autoimmune and inflammatory disorders: potential and challenges," Trends in Pharmacological Sciences (2007) 28(3):142-148.

(Continued)

*Primary Examiner* — Rayna Rodriguez
(74) *Attorney, Agent, or Firm* — MORRISON & FOERSTER LLP

(57) ABSTRACT

The present invention pertains to the treatment of diseases associated with a dysregulated immune response such as auto immune disorders, inflammatory diseases or pathological immune responses as adverse effects of medical treatments. In particular the invention provides a combined use of inhibitors of Receptor-interacting serine/threonine-protein kinase (RIPK1) and inhibitors of Inhibitor of κB (IκB) Kinase (IKK) in subjects suffering from such disorders. The invention provides such inhibitory compounds and their combinations for use in medical applications, as well as pharmaceutical compositions comprising the compounds of the invention.

13 Claims, 7 Drawing Sheets

Figure 1A:
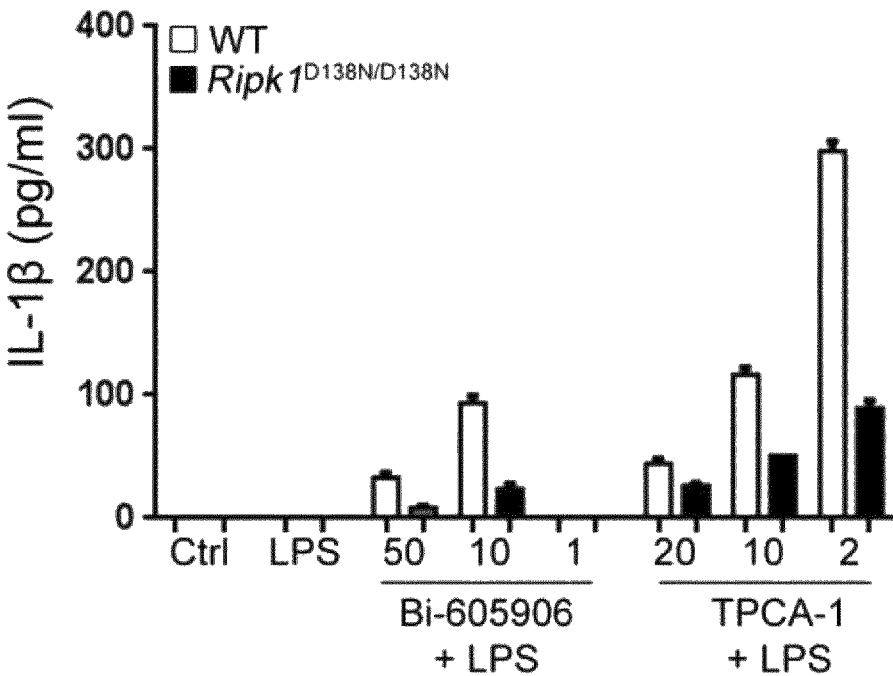

Specification includes a Sequence Listing.

(56)     References Cited

OTHER PUBLICATIONS

Yona et al., "Fate Mapping Reveals Origins and Dynamics of Monocytes and Tissue Macrophages Under Homeostasis," Immunity (2013) 38(1):79-91.

Zandi et al., "The IkappaB Kinase Complex (IKK) Contains Two Kinase Subunits, IKKalpha and IKKbeta, Necessary for IkappaB Phosphorylation and NF-kappaB Activation," Cell (1997) 91(2):243-252.

Gosset et al., "Expression of E-Selectin, ICAM-1 and VCAM-1 on Bronchial Biopsies from Allergic and Non-Allergic Asthmatic Patients," Int Arch Allergy Immunol (1995) 106:69-77.

Hsu et al., "IL-1β-driven neutrophilla preserves antibacterial defense in the absence of the kinase IKKβ," Nature Immunology (2011) 12:144-150.

Koch et al., "Angiogenesis mediated by soluble forms of E-selectin and vascular cell adhesion molecule-1," Nature (1995) 376:517-519.

Koren et al., "Immune Responses to Therapeutic Proteins in Humans—Clinical Significance, Assessment and Prediction," Curr Pharm Biotechnol (2002) 3:349.

Li et al., "Severe Liver Degeneration in Mice Lacking the IκB Kinase 2 Gene," Science (1999) 284(5412):321-325.

Panes et al., "Regional differences in constitutive and induced ICAM-1 expression in vivo," Am J Physiol (1995) 269 (6):H1955-H1964.

Zwacka et al., "Redox gene therapy for ischemia/reperfusion injury of the liver reduces AP1 and NF-κB activation," Nature Medicine (1998) 4:698-704.

Kumari et al., "Role of RIP kinase signalling in the development of skin inflammation in mice with keratinocyte-specific IKX deficiency," Journal of Investigative Dermatology (2016) 136:S218 Abstract 334.

Kondylis, "RIPK1 and allies in the battle against hepatocyte apoptosis and liver cancer," Transl Cancer Res. (2017) 6: S569-77.

* cited by examiner

IKK2<sup>K44A/WT</sup> RIPK1<sup>D138N/D138N</sup>   x   IKK2<sup>K44A/WT</sup> RIPK1<sup>D138N/D138N</sup>

| Litter # | Litter size | K44A/K44A |
|---|---|---|
| 1 | 6 | 1 |
| 2 | 7 | 4 |
| 3 | 10 | 5 |
| 4 | 8 | 3 |
| 5 | 6 | 1 |
| Total: | 37 | 14 |

IKK2<sup>K44A/WT</sup> x IKK2<sup>K44A/WT</sup>

| Litter # | Litter size | K44A/K44A |
|---|---|---|
| 1 | 4 | 0 |
| 2 | 7 | 0 |
| 3 | 2 | 0 |
| 4 | 2 | 0 |
| 5 | 5 | 0 |
| 6 | 6 | 0 |
| 7 | 8 | 0 |
| 8 | 6 | 0 |
| 9 | 8 | 0 |
| 10 | 7 | 0 |
| Total: 10 | 55 | 0 |

Figure 2b

SEQUENCE LISTING

```
<160> NUMBER OF SEQ ID NOS: 7

<210> SEQ ID NO 1
<211> LENGTH: 671
<212> TYPE: PRT
<213> ORGANISM: Homo sapiens

<400> SEQUENCE: 1

Met Gln Pro Asp Met Ser Leu Asn Val Ile Lys Met Lys Ser Ser Asp
1               5                   10                  15

Phe Leu Glu Ser Ala Glu Leu Asp Ser Gly Gly Phe Gly Lys Val Ser
            20                  25                  30

Leu Cys Phe His Arg Thr Gln Gly Leu Met Ile Met Lys Thr Val Tyr
        35                  40                  45

Lys Gly Pro Asn Cys Ile Glu His Asn Glu Ala Leu Leu Glu Glu Ala
    50                  55                  60

Lys Met Met Asn Arg Leu Arg His Ser Arg Val Val Lys Leu Leu Gly
65                  70                  75                  80

Val Ile Ile Glu Glu Gly Lys Tyr Ser Leu Val Met Glu Tyr Met Glu
                85                  90                  95

Lys Gly Asn Leu Met His Val Leu Lys Ala Glu Met Ser Thr Pro Leu
            100                 105                 110

Ser Val Lys Gly Arg Ile Ile Leu Glu Ile Ile Glu Gly Met Cys Tyr
            115                 120                 125

Leu His Gly Lys Gly Val Ile His Lys Asp Leu Lys Pro Glu Asn Ile
        130                 135                 140

Leu Val Asp Asn Asp Phe His Ile Lys Ile Ala Asp Leu Gly Leu Ala
145                 150                 155                 160

Ser Phe Lys Met Trp Ser Lys Leu Asn Asn Glu Glu His Asn Glu Leu
                165                 170                 175

Arg Glu Val Asp Gly Thr Ala Lys Lys Asn Gly Gly Thr Leu Tyr Tyr
            180                 185                 190

Met Ala Pro Glu His Leu Asn Asp Val Asn Ala Lys Pro Thr Glu Lys
```

-continued

```
              195                  200                  205

Ser Asp Val Tyr Ser Phe Ala Val Val Leu Trp Ala Ile Phe Ala Asn
    210                  215                  220

Lys Glu Pro Tyr Glu Asn Ala Ile Cys Glu Gln Gln Leu Ile Met Cys
225                  230                  235                  240

Ile Lys Ser Gly Asn Arg Pro Asp Val Asp Ile Thr Glu Tyr Cys
                245                  250                  255

Pro Arg Glu Ile Ile Ser Leu Met Lys Leu Cys Trp Glu Ala Asn Pro
                260                  265                  270

Glu Ala Arg Pro Thr Phe Pro Gly Ile Glu Glu Lys Phe Arg Pro Phe
                275                  280                  285

Tyr Leu Ser Gln Leu Glu Glu Ser Val Glu Glu Asp Val Lys Ser Leu
    290                  295                  300

Lys Lys Glu Tyr Ser Asn Glu Asn Ala Val Val Lys Arg Met Gln Ser
305                  310                  315                  320

Leu Gln Leu Asp Cys Val Ala Val Pro Ser Ser Arg Ser Asn Ser Ala
                325                  330                  335

Thr Glu Gln Pro Gly Ser Leu His Ser Ser Gln Gly Leu Gly Met Gly
                340                  345                  350

Pro Val Glu Glu Ser Trp Phe Ala Pro Ser Leu Glu His Pro Gln Glu
                355                  360                  365

Glu Asn Glu Pro Ser Leu Gln Ser Lys Leu Gln Asp Glu Ala Asn Tyr
    370                  375                  380

His Leu Tyr Gly Ser Arg Met Asp Arg Gln Thr Lys Gln Gln Pro Arg
385                  390                  395                  400

Gln Asn Val Ala Tyr Asn Arg Glu Glu Glu Arg Arg Arg Arg Val Ser
                405                  410                  415

His Asp Pro Phe Ala Gln Gln Arg Pro Tyr Glu Asn Phe Gln Asn Thr
                420                  425                  430

Glu Gly Lys Gly Thr Ala Tyr Ser Ser Ala Ala Ser His Gly Asn Ala
                435                  440                  445

Val His Gln Pro Ser Gly Leu Thr Ser Gln Pro Gln Val Leu Tyr Gln
    450                  455                  460

Asn Asn Gly Leu Tyr Ser Ser His Gly Phe Gly Thr Arg Pro Leu Asp
465                  470                  475                  480

Pro Gly Thr Ala Gly Pro Arg Val Trp Tyr Arg Pro Ile Pro Ser His
                485                  490                  495

Met Pro Ser Leu His Asn Ile Pro Val Pro Glu Thr Asn Tyr Leu Gly
                500                  505                  510

Asn Thr Pro Thr Met Pro Phe Ser Ser Leu Pro Pro Thr Asp Glu Ser
                515                  520                  525

Ile Lys Tyr Thr Ile Tyr Asn Ser Thr Gly Ile Gln Ile Gly Ala Tyr
    530                  535                  540

Asn Tyr Met Glu Ile Gly Gly Thr Ser Ser Ser Leu Leu Asp Ser Thr
545                  550                  555                  560

Asn Thr Asn Phe Lys Glu Glu Pro Ala Ala Lys Tyr Gln Ala Ile Phe
                565                  570                  575

Asp Asn Thr Thr Ser Leu Thr Asp Lys His Leu Asp Pro Ile Arg Glu
                580                  585                  590

Asn Leu Gly Lys His Trp Lys Asn Cys Ala Arg Lys Leu Gly Phe Thr
                595                  600                  605

Gln Ser Gln Ile Asp Glu Ile Asp His Asp Tyr Glu Arg Asp Gly Leu
    610                  615                  620
```

-continued

```
Lys Glu Lys Val Tyr Gln Met Leu Gln Lys Trp Val Met Arg Glu Gly
625                 630                 635                 640

Ile Lys Gly Ala Thr Val Gly Lys Leu Ala Gln Ala Leu His Gln Cys
                645                 650                 655

Ser Arg Ile Asp Leu Leu Ser Ser Leu Ile Tyr Val Ser Gln Asn
                660                 665                 670

<210> SEQ ID NO 2
<211> LENGTH: 756
<212> TYPE: PRT
<213> ORGANISM: Homo sapiens

<400> SEQUENCE: 2

Met Ser Trp Ser Pro Ser Leu Thr Thr Gln Thr Cys Gly Ala Trp Glu
1               5                   10                  15

Met Lys Glu Arg Leu Gly Thr Gly Gly Phe Gly Asn Val Ile Arg Trp
                20                  25                  30

His Asn Gln Glu Thr Gly Glu Gln Ile Ala Ile Lys Gln Cys Arg Gln
            35                  40                  45

Glu Leu Ser Pro Arg Asn Arg Glu Arg Trp Cys Leu Glu Ile Gln Ile
        50                  55                  60

Met Arg Arg Leu Thr His Pro Asn Val Val Ala Ala Arg Asp Val Pro
65                  70                  75                  80

Glu Gly Met Gln Asn Leu Ala Pro Asn Asp Leu Pro Leu Leu Ala Met
                85                  90                  95

Glu Tyr Cys Gln Gly Gly Asp Leu Arg Lys Tyr Leu Asn Gln Phe Glu
                100                 105                 110

Asn Cys Cys Gly Leu Arg Glu Gly Ala Ile Leu Thr Leu Leu Ser Asp
            115                 120                 125

Ile Ala Ser Ala Leu Arg Tyr Leu His Glu Asn Arg Ile Ile His Arg
        130                 135                 140

Asp Leu Lys Pro Glu Asn Ile Val Leu Gln Gln Gly Glu Gln Arg Leu
145                 150                 155                 160

Ile His Lys Ile Ile Asp Leu Gly Tyr Ala Lys Glu Leu Asp Gln Gly
                165                 170                 175

Ser Leu Cys Thr Ser Phe Val Gly Thr Leu Gln Tyr Leu Ala Pro Glu
                180                 185                 190

Leu Leu Glu Gln Gln Lys Tyr Thr Val Thr Val Asp Tyr Trp Ser Phe
            195                 200                 205

Gly Thr Leu Ala Phe Glu Cys Ile Thr Gly Phe Arg Pro Phe Leu Pro
        210                 215                 220

Asn Trp Gln Pro Val Gln Trp His Ser Lys Val Arg Gln Lys Ser Glu
225                 230                 235                 240

Val Asp Ile Val Val Ser Glu Asp Leu Asn Gly Thr Val Lys Phe Ser
                245                 250                 255

Ser Ser Leu Pro Tyr Pro Asn Asn Leu Asn Ser Val Leu Ala Glu Arg
                260                 265                 270

Leu Glu Lys Trp Leu Gln Leu Met Leu Met Trp His Pro Arg Gln Arg
            275                 280                 285

Gly Thr Asp Pro Thr Tyr Gly Pro Asn Gly Cys Phe Lys Ala Leu Asp
        290                 295                 300

Asp Ile Leu Asn Leu Lys Leu Val His Ile Leu Asn Met Val Thr Gly
305                 310                 315                 320

Thr Ile His Thr Tyr Pro Val Thr Glu Asp Glu Ser Leu Gln Ser Leu
```

-continued

```
                 325             330             335

Lys Ala Arg Ile Gln Gln Asp Thr Gly Ile Pro Glu Glu Asp Gln Glu
            340             345             350

Leu Leu Gln Glu Ala Gly Leu Ala Leu Ile Pro Asp Lys Pro Ala Thr
            355             360             365

Gln Cys Ile Ser Asp Gly Lys Leu Asn Glu Gly His Thr Leu Asp Met
        370             375             380

Asp Leu Val Phe Leu Phe Asp Asn Ser Lys Ile Thr Tyr Glu Thr Gln
    385             390             395             400

Ile Ser Pro Arg Pro Gln Pro Glu Ser Val Ser Cys Ile Leu Gln Glu
                405             410             415

Pro Lys Arg Asn Leu Ala Phe Phe Gln Leu Arg Lys Val Trp Gly Gln
            420             425             430

Val Trp His Ser Ile Gln Thr Leu Lys Glu Asp Cys Asn Arg Leu Gln
            435             440             445

Gln Gly Gln Arg Ala Ala Met Met Asn Leu Leu Arg Asn Asn Ser Cys
        450             455             460

Leu Ser Lys Met Lys Asn Ser Met Ala Ser Met Ser Gln Gln Leu Lys
    465             470             475             480

Ala Lys Leu Asp Phe Phe Lys Thr Ser Ile Gln Ile Asp Leu Glu Lys
                485             490             495

Tyr Ser Glu Gln Thr Glu Phe Gly Ile Thr Ser Asp Lys Leu Leu Leu
            500             505             510

Ala Trp Arg Glu Met Glu Gln Ala Val Glu Leu Cys Gly Arg Glu Asn
            515             520             525

Glu Val Lys Leu Leu Val Glu Arg Met Met Ala Leu Gln Thr Asp Ile
        530             535             540

Val Asp Leu Gln Arg Ser Pro Met Gly Arg Lys Gln Gly Gly Thr Leu
    545             550             555             560

Asp Asp Leu Glu Glu Gln Ala Arg Glu Leu Tyr Arg Arg Leu Arg Glu
                565             570             575

Lys Pro Arg Asp Gln Arg Thr Glu Gly Asp Ser Gln Glu Met Val Arg
            580             585             590

Leu Leu Leu Gln Ala Ile Gln Ser Phe Glu Lys Lys Val Arg Val Ile
            595             600             605

Tyr Thr Gln Leu Ser Lys Thr Val Val Cys Lys Gln Lys Ala Leu Glu
        610             615             620

Leu Leu Pro Lys Val Glu Glu Val Val Ser Leu Met Asn Glu Asp Glu
    625             630             635             640

Lys Thr Val Val Arg Leu Gln Glu Lys Arg Gln Lys Glu Leu Trp Asn
                645             650             655

Leu Leu Lys Ile Ala Cys Ser Lys Val Arg Gly Pro Val Ser Gly Ser
            660             665             670

Pro Asp Ser Met Asn Ala Ser Arg Leu Ser Gln Pro Gly Gln Leu Met
            675             680             685

Ser Gln Pro Ser Thr Ala Ser Asn Ser Leu Pro Glu Pro Ala Lys Lys
        690             695             700

Ser Glu Glu Leu Val Ala Glu Ala His Asn Leu Cys Thr Leu Leu Glu
    705             710             715             720

Asn Ala Ile Gln Asp Thr Val Arg Glu Gln Asp Gln Ser Phe Thr Ala
                725             730             735

Leu Asp Trp Ser Trp Leu Gln Thr Glu Glu Glu Glu His Ser Cys Leu
            740             745             750
```

-continued

```
Glu Gln Ala Ser
        755

<210> SEQ ID NO 3
<211> LENGTH: 82
<212> TYPE: DNA
<213> ORGANISM: Homo sapiens

<400> SEQUENCE: 3
gcgacaggtg aacagatcgc catcaagcaa tgccgacagg agctcagccc aaagaacaga        60
gaccgctggt gcctcgaaat cc                                                 82

<210> SEQ ID NO 4
<211> LENGTH: 83
<212> TYPE: DNA
<213> ORGANISM: Homo sapiens

<400> SEQUENCE: 4
gcgacaggtg aacagatcgc catcgcgcaa tgccgacagg agctcagccc aaagaacaga        60
gaccgctggt gcctcgaaat cca                                                83

<210> SEQ ID NO 5
<211> LENGTH: 28
<212> TYPE: PRT
<213> ORGANISM: Homo sapiens

<400> SEQUENCE: 5

Ala Thr Gly Glu Gln Ile Ala Ile Lys Gln Cys Arg Gln Glu Leu Ser
1               5                   10                  15

Pro Lys Asn Arg Asp Arg Trp Cys Leu Glu Ile Gln
            20                  25

<210> SEQ ID NO 6
<211> LENGTH: 11
<212> TYPE: DNA
<213> ORGANISM: Homo sapiens

<400> SEQUENCE: 6
catcaagcaa t                                                            11

<210> SEQ ID NO 7
<211> LENGTH: 11
<212> TYPE: DNA
<213> ORGANISM: Homo sapiens

<400> SEQUENCE: 7
catcgcgcaa t                                                            11
```

COMBINATIONS OF RIPK₁- AND IKK-INHIBITORS FOR THE PREVENTION OR TREATMENT OF IMMUNE DISEASES

CROSS REFERENCE TO RELATED APPLICATIONS

This application is a national stage application under 35 U.S.C. § 371 of International Application No. PCT/EP2018/084055, filed internationally on Dec. 7, 2018, which claims the benefit of priority to European Application No. 17205864.6, filed Dec. 7, 2017.

SUBMISSION OF SEQUENCE LISTING ON ASCII TEXT FILE

The present application is being filed along with a Sequence Listing in electronic format. The Sequence Listing is provided as a file entitled 595282002400SeqList.txt, created Jun. 1, 2020 which 13,732 bytes in size. The information in the electronic format of the Sequence Listing is incorporated by reference in its entirety.

FIELD OF THE INVENTION

The present invention pertains to the treatment of diseases associated with a dysregulated immune response such as auto immune disorders, inflammatory diseases or pathological immune responses as adverse effects of medical treatments. In particular the invention provides a combined use of inhibitors of Receptor-interacting serine/threonine-protein kinase 1 (RIPK₁) and inhibitors of Inhibitor of κB (IκB) Kinase (IKK) in subjects suffering from such disorders. The invention provides such inhibitory compounds and their combinations for use in medical applications, as well as pharmaceutical compositions comprising the compounds of the invention.

DESCRIPTION

NF-κB is a heterodimeric transcription factor that regulates the expression of multiple inflammatory genes. NF-κB has been implicated in many pathophysiologic processes including angiogenesis (Koch et al, Nature 1995, 376, 517-519), atherosclerosis (Brand et al. Clin Inv. 1996, 97, 1715-1722), endotoxic shock and sepsis (Bohrer et al, J. Clin. Inv. 1997, 200972-985), inflammatory bowel disease (Panes et al, Am J Physiol. 1995, 269, H1955-H1964), is-chemia/reperfusion injury (Zwacka et al, Nature Medicine 1998, 4, 698-704), and allergic lung inflammation (Gosset et al, Int Arch Allergy Immunol. 1995, 206, 69-77). Thus the inhibition of NF-κB by targeting regulatory proteins in the NF-κB activation pathway represents an attractive strategy for generating therapeutics for the treatment of dysregulated immune responses due to NF-κB's central role in inflammatory conditions.

The IκB kinases (IKKs) are key regulatory signaling molecules that coordinate the activation of NF-κB. Many immune and inflammatory mediators including TNFα, lipopolysaccharide (LPS), IL-1β, CD3/CD28 (antigen presentation), CD40L, FasL viral infection, and oxidative stress have been shown to lead to NF-κB activation. Although the receptor complexes that transduce these diverse stimuli appear very different in their protein components, it is understood that each of these stimulation events leads to activation of the IKKs and NF-κB.

The IKK complex, composed of the regulatory subunit NEMO/IKKγ and the catalytic subunits IKKα/IKK₁ and IKKβ/IKK₂ is essential for activation of NF-κB. The IKK/NF-Kβ signalling pathway is a key regulator of inflammatory responses. Therefore, inhibitors of IKK/NF-κB signalling have a great potential for the treatment of inflammatory diseases. However, inhibition of IKK/NF-κB signalling in myeloid cells, either genetically (IKKβ knockout) or pharmacologically (small molecule IKK inhibitors), resulted in increased production of IL-1β and systemic neutrophilia (Greten et al, DOL10.1016/j.ce11.2007.07.009, Hsu et al, DOL: 10.1038/ni.1976). These findings raised serious concerns about the safety of IKK/NF-κB signalling inhibitors, which made several companies terminate their programs for the development and therapeutic application of IKK inhibitors. In addition, previous studies showing that inhibition of IKK signalling in epithelial cells of the intestine and the skin and in liver parenchymal cells caused severe inflammatory disease in these tissues, raised additional concerns about the safety of IKK inhibitors (Pasparakis et al, DOI:10.10381nature00820, Nenci et al, DOI:10.1038/nature05698, Luedde et al, DOI:10.1016/j.ccr.2006.12.016).

Hence, the present invention seeks to provide novel therapeutic approaches to tackle immune related disorders via inhibition of IKK/NF-κB signaling, but overcoming known adverse effects of such treatments.

The above problem is solved in a first aspect by a Receptor-interacting serine/threonine-protein kinase 1 (RIPK₁) inhibitor for use in the treatment or prevention of a disease associated with a pathological or deregulated immune response, such as an increased Interleukin-1β (IL-1β) release or systemic neutrophilia, in a subject.

Without being bound to theory, the inventors surmised that an increased production of IL-1 beta by myeloid cells treated with IKK inhibitors depends largely on RIPK₁ kinase activity. Inhibition of RIPK₁ kinase activity either genetically (using knock-in mice expressing kinase-inactive RIPK₁ D138N) or pharmacologically (using Necrostatin-1, a chemical inhibitor of RIPK₁) strongly diminished the LPS-induced production of IL-1β by macrophages treated with two different IKK inhibitors. This demonstrates that the most serious known side effect of IKK inhibitors, namely the increased production of IL-1β by myeloid cells, can be prevented by the inhibition of RIPK₁. Hence, the invention surprisingly discovered the application of RIPK₁ inhibitors in the treatment of diseases associated with a pathological or deregulated immune response, such as an increased Interleukin-1β (IL-1β) release induced by IKK inhibition.

Thus, in some preferred embodiments the disease associated with an increased IL-1β release or systemic neutrophilia is aside effector adverse effect caused by a treatment of the subject with an Inhibitor of κB (IκB) Kinase (IKK)/Nuclear Factor κB (NFκB)—signaling inhibitor.

The term "RIPK₁ inhibitor" or "inhibitor of RIPK₁" or "antagonist of RIPK₁" or any similar expressions shall in context of the present invention encompass any compound or combination of compounds that have an activity as a modulator of the expression, function and/or stability of RIPK₁, or of a variant of RIPK₁.

In context of the invention a modulator is preferably an inhibitor/antagonist.

Further, in context of the present invention the term "receptor interacting serine/threonine kinase 1" or "RIPK₁" pertains to a human gene encoding for a protein according to the amino acid sequence shown in SEQ ID NO: 1. RIPK₁ is also known as "receptor (TNFRSF)-interacting serine-threonine kinase 1" or "receptor-interacting protein kinase 1" (RIP) (HUGO Gene Nomenclature Committee symbol: HGNC:10019, database version of November 2017). The human $RIPK_1$ gene is located 6p25.2, homologs are known from mouse (MGI:108212; NCBI Gene: 19766) and rat (Rat Genome Database (RGD) ID: 1310158).

The terms "$RIPK_1$-protein" or "protein of $RIPK_1$," as used in context of the herein disclosed invention shall pertain to a protein (such as a full-length protein, fusion protein or partial protein) comprising a sequence as shown in SEQ ID NO: 1. The terms shall also refer to a protein comprising the amino acid sequence according to SEQ ID NO: 1 with any protein modifications. Such protein modifications preferably do not alter the amino acid sequence of the polypeptide chain, but constitute a functional group, which is conjugated to the basic amino acid polymer chain. Protein modifications in context of the invention may be selected from a conjugation of additional amino acid sequences to the $RIPK_1$ amino acid chain, such as ubiquitination, sumolation, neddylation, or similar small protein conjugates. Other protein modifications include, but are not limited to, glycosylation, methylation, lipid-conjugation, or other natural or artificial post-translational modifications known to the skilled person. The terms "protein of a variant of $RIPK_1$" and the like, shall have the corresponding meaning with respect to a variant of $RIPK_1$.

The terms "$RIPK_1$-mRNA" or "mRNA of $RIPK_1$," as used in context of the herein disclosed invention shall pertain to a messenger ribonucleic acid (such as a full-length mRNA, fusion mRNA or partial mRNA, and/or splice-variants thereof) comprising a region encoding for an amino acid sequence as shown in SEQ ID NO: 1. The terms shall also refer to an mRNA comprising a region encoding for the amino acid sequence according to SEQ ID NO: 1 with any codon or nucleotide modifications. Such modifications preferably would not alter the amino acid sequence of the encoded polypeptide chain. The terms "mRNA of a variant of $RIPK_1$" and the like, shall have the corresponding meaning with respect to a variant of $RIPK_1$.

A variant of $RIPK_1$ is, in some embodiments, a protein comprising an amino acid sequence having at least 60%, 70%, 80%, 90%, preferably at least 80% such as at least 90% sequence identity to SEQ ID NO: 1, and most preferably at least 95% (such as at least 98%) sequence identity to SEQ ID NO: 1 (the human $RIPK_1$ amino acid sequence). In one preferred embodiment of the invention, the variant of $RIPK_1$ comprises an amino acid sequence with at least 80% sequence identity to the amino acid sequence shown in SEQ ID NO: 1.

As used herein, the terms "identical" or percent "identity", when used anywhere herein in the context of two or more nucleic acid or protein/polypeptide sequences, refer to two or more sequences or subsequences that are the same or have (or have at least) a specified percentage of amino acid residues or nucleotides that are the same (i.e., at, or at least, about 60% identity, preferably at, or at least, 65%, 70%, 75%, 80%, 85%, 90%, 91%, 92%, 93% or 94%, identity, and more preferably at, or at least, about 95%, 96%, 97%, 98%, 99%, or higher identity over a specified region—preferably over their full length sequences—, when compared and aligned for maximum correspondence over the comparison window or designated region) as measured using a sequence comparison algorithms, or by manual alignment and visual inspection (see, e.g., NCBI web site). In particular for amino acid identity, those using BLASTP 2.2.28+ with the following parameters: Matrix: BLOSUM62; Gap Penalties: Existence: 11, Extension: 1; Neighboring words threshold 11; Window for multiple hits: 40.

In context of the present invention the term "subject" or "patient" preferably refers to a mammal, such as a mouse, rat, guinea pig, rabbit, cat, dog, monkey, or preferably a human, for example a human patient. The subject of the invention may be at danger of suffering from a dysregulated immune response, preferably induced or caused by the administration of a IKK inhibitor as defined herein elsewhere.

A "modulator of expression, function and/or stability of $RIPK_1$ or IKK, or of a variant of $RIPK_1$ or IKK", or grammatically similar expressions, in context of the invention may be any compound that affects, for example when an inhibitor/antagonist impairs or interferes with, the expression, function and/or stability of $RIPK_1$ or IKK respectively, or of a variant of these targets, in particular the expression, function and/or stability of protein of $RIPK_1$ or IKK or their variant, and/or the expression, function and/or stability of mRNA of $RIPK_1$ or IKK or their variant.

In context of the present invention the $RIPK_1$ inhibitor is selected from a small molecule, a polypeptide, peptide, glycoprotein, a peptide-mimetic, an antigen binding protein (ABP)(for example, an antibody, antibody-like molecule or other antigen binding derivative, or an or antigen binding fragment thereof), a nucleic acid such as a DNA or RNA, for example an antisense or inhibitory DNA or RNA, a ribozyme, an RNA or DNA aptamer, RNAi, siRNA, shRNA and the like, including variants or derivatives thereof such as a peptide nucleic acid (PNA), a genetic construct for targeted gene editing, such as a CRISPR/Cas9 construct and/or a guide nucleic acid (gRNA or gDNA) and/or tracrRNA In another preferred embodiment the modulator of expression, function and/or stability of $RIPK_1$, or of a variant of $RIPK_1$, is an anti-sense nucleotide molecule such as described in detail herein below, more preferably one that binds to, such as specifically binds to, a nucleic acid that encodes or regulates the expression of $RIPK_1$, or of a variant of $RIPK_1$, or alternatively more preferably one that binds to, such as specifically bind to, a nucleic acid that encodes or (regulates the expression of a gene that controls the expression, function and/or stability of) $RIPK_1$, or of a variant of $RIPK_1$.

As used herein, the terms "inhibitor of $RIPK_1$ expression" and the like (including similarly, "antagonist of $RIPK_1$ expression" and the like) shall relate to any of the herein disclosed modulators (for example, the antigen binding constructs or anti-sense molecules described herein), which has an antagonistic activity toward the expression of an $RIPK_1$ protein, such that it impairs, suppresses, reduces and/or lowers the expression of an $RIPK_1$ protein such as may be determined by measuring an amount (or change in an amount) of $RIPK_1$ protein or $RIPK_1$ mRNA. The term "expression" means in this context the cellular process of transcribing a gene into an mRNA and the following translation of the mRNA into a protein. "Gene expression" therefore may refer only to the generation of mRNA, irrespectively from the fate of the so produced mRNA, or alternatively/additionally to the translation of the expressed mRNA into a protein. The term "protein expression" on the other hand shall refer to the complete cellular process of synthesis of proteins. In one preferred example, an inhibiting modulator of the invention, such as an anti-sense molecule, may bind to the $RIPK_1$ gene or mRNA and reduce transcription and/or translation or the $RIPK_1$ mRNA. The terms "inhibitor of expression of a variant of $RIPK_1$" and the like, shall have the corresponding meaning with respect to a variant of $RIPK_1$.

The terms "inhibitor of $RIPK_1$ stability" and the like (including similarly, "antagonist of $RIPK_1$ stability" and the like) shall refer to any of the herein disclosed modulators (for ex-ample, the antigen binding constructs or anti-sense molecules described herein), which has a negative activity towards the stability of an $RIPK_1$ protein.

The terms an "inhibitor of $RIPK_1$ function" and the like (including similarly, "antagonist of $RIPK_1$ function" and the like) shall refer to any of the herein disclosed modulators (for example, the antigen binding constructs or anti-sense molecules described herein) that impairs, such as induces a decrease or reduction in the amount or rate of one or more activities of $RIPK_1$ protein or mRNA (for example, by impairing the expression and/or stability of $RIPK_1$ protein or mRNA), such as one or more of those activities described herein, for ex-ample, the kinase activity of $RIPK_1$.

Such an inhibiting modulator can act directly, for example, by binding to $RIPK_1$ and decreasing the amount or rate of one or more of the properties of $RIPK_1$ such as its expression, function and/or stability. An $RIPK_1$ antagonist or inhibitor can also decrease the amount or rate of $RIPK_1$ function or activity by impairing its expression, stability, for example, by binding to $RIPK_1$ protein or mRNA and modifying it, such as by removal or addition of a moiety, or altering its three-dimensional conformation; and by binding to $RIPK_1$ protein or mRNA and reducing its stability or conformational integrity. An $RIPK_1$ antagonist or inhibitor can also act indirectly, for example, by binding to a regulatory molecule or gene region to modulate regulatory protein or gene region function and affect a decrease in the amount or rate of $RIPK_1$ expression, function and/or stability, in particular by impairing one or more activity of $RIPK_1$ protein or mRNA (such as by changing the amount or rate of expression and/or stability of $RIPK_1$ protein or mRNA). Thus, an $RIPK_1$ inhibitor or antagonist can act by any mechanisms that impair, such as result in a decrease in, the amount or rate of $RIPK_1$ expression, function and/or stability.

In some preferred embodiments it might be preferred that the $RIPK_1$ inhibitor is a compound that only affects and impairs the kinase enzymatic activity or function of $RIPK_1$ without interfering with $RIPK_1$ protein expression or protein stability. The term "kinase activity" as used herein refers to a phosphorylation of a substrate including $RIPK_1$ by $RIPK_1$ protein. Such embodiments might be advantageous, because $RIPK_1$ is known to exert kinase independent functions the impairment of which could induce or cause additional undesirable adverse effects in a treated subject or patient. In order to specifically target and reduce/inhibit $RIPK_1$ kinase activity, the present invention in some preferred embodiments pertains to compounds which selectively bind to and impair kinase enzymatic activity or the autophosphorylation of $RIPK_1$ or the acquisition of conformational changes induced by autophosphorylation, such as small molecular compounds, for example kinase inhibitors.

Preferred $RIPK_1$ inhibitors of the invention are small molecular compounds. Such compounds are preferably selected from GSK2982772, necrostatin-1 (5-(1H-indo1-3-ylmethyl)-3-methyl-2-thioxo-4-imidazolidinone, 5-(indo1-3-ylmethyl)-3-methyl-2-thio-hydantoin) and necrostatin-1 stable (5-((7-chloro-1H-indol-3-yl)methyl)-3-methyl-2,4-imidazolidinedione, 5-((7-chloro-1H-indol-3-yl)methyl)-3-methylimidazolidine-2,4-dione). However, any other known $RIPK_1$ inhibitor may be used in context of the invention.

As will be further described herein, the subject or patient subjected to the treatments or uses of the invention in preferred embodiments is suffering from a disease associated with a dysregulated immune response such as auto immune disorders, inflammatory diseases or pathological immune responses as adverse effects of medical treatments. Treatment or prevention in some embodiments comprises the administration of a therapeutically effective amount of the $RIPK_1$ inhibitor to the subject. Such an administration may be a sequential or concomitant administration of a therapeutically effective amount of both the $RIPK_1$ inhibitor and an IKK/NFκB signaling inhibitor to the subject.

As used herein, the term "therapeutically effective amount" means that amount of a compound or combination that will elicit the biological or medical response of a tissue, system, animal or human subject that is being sought, for instance, by a researcher or clinician, in accordance with the herein disclosed invention. Furthermore, the term "therapeutically effective amount" means any amount which, as compared to a corresponding subject who has not received such amount, results in improved treatment, healing, prevention, or amelioration f a disease, disorder, or side effect, or a decrease in the rate of advancement of a disease or disorder.

In accordance with all aspects and embodiments of the medical uses and methods of treatment provided herein, the effective amount of the compounds or combinations administered at least once to a subject in need of treatment with a $RIPK_1$ and/or IKK/NFκB signaling inhibitor is, typically, between about 0.01 mg/kg and about 500 mg/kg per administration, or about 0.01 mg/kg and about 100 mg/kg per administration such as between about 1 mg/kg and about 10 mg/kg per administration. In some embodiments, the effective amount administered at least once to said subject of a $RIPK_1$ and/or IKK/NFκB signaling inhibitor is between about 0.01 mg/kg and about 0.1 mg/kg per administration, between about 0.1 mg/kg and about 1 mg/kg per administration, between about 1 mg/kg and about 5 mg/kg per administration, between about 5 mg/kg and about 10 mg/kg per administration, between about 10 mg/kg and about 50 mg/kg per administration, or between about 50 mg/kg and about 100 mg/kg per administration.

For the prevention or treatment of disease, the appropriate dosage of a $RIPK_1$ and/or IKK/NFκB signaling inhibitor (or a pharmaceutical composition comprised thereof) will depend on the type of disease to be treated, the severity and course of the disease, whether the $RIPK_1$ and/or IKK/NFκB signaling inhibitor and/or pharmaceutical composition is administered for preventive or therapeutic purposes, previous therapy, the patient's clinical history, age, size/weight and response to the $RIPK_1$ and/or IKK/NFκB signaling inhibitor and/or pharmaceutical composition, and the discretion of the attending physician. The $RIPK_1$ and/or IKK/NFκB signaling inhibitor and/or pharmaceutical composition is suitably administered to the patient at one time or over a series of treatments. If such $RIPK_1$ and/or IKK/NFκB signaling inhibitor and/or pharmaceutical composition is administered over a series of treatments, the total number of administrations for a given course of treatment may consist of a total of about 2, 3, 4, 5, 6, 7, 8, 9, 10 or more than about 10 treatments. For example, a treatment may be given once every day (or 2, 3 or 4 times a day) for a week, a month or even several months. In certain embodiments, the course of treatment may continue indefinitely.

The term "IKK inhibitor" is used in the broadest sense and includes any molecule that partially or fully blocks, inhibits or neutralizes a biological activity mediated by IKK, preferably by preventing the activation of IKK. The aforesaid with regard to the nature and definition of inhibitors of $RIPK_1$ in context of the invention shall equally apply to the nature and definition of "IKK inhibitors". In addition thereto, preferred IKK inhibitors act directly on one or more subunits of IKK for example by binding to one or more subunits of IKK. However, in other embodiments the IKK inhibitors may prevent IKK from interacting with a substrate, such as I-κB and/or may act on molecules in an IKK signaling pathway, preferably downstream from IKK. In still other embodiments the IKK inhibitors may modulate the level of IKK gene expression or otherwise reduce the levels of IKK in affected cells. The ability of a molecule to inhibit IKK activation can be measured using assays that are well known in the art. For example and without limitation, IKK inhibitors can be identified using immune complex kinase assays and gene reporter assays. Briefly, in an immune complex kinase assay, immunoprecipitated IKK complexes are examined for the ability to phosphorylate GST-IκBα invitro. For example, IKK complexes can be immunoprecipitated from cleared striatal extracts from animals or cells treated with the putative IKK inhibitor by incubation with a mouse anti-IKKα antibody (Santa Cruz Biotechnology) coupled to protein-A beads and rocked for 3 hr at 4° C. Beads are washed, and IKK activity can be evaluated invitro with 1 μg of purified GST-Iκ-Bα (N-terminal 61 amino acids) in the presence of 10 μCi of [32P]γ-ATP for 30 min at 30° C. Products are examined by SDS-PAGE followed by autoradiography.

Furthermore, the term "IKK inhibitor" includes any molecule that mimics a biological activity mediated by an IKK subunit and specifically changes the function or expression of IKK, or the efficiency of signaling through IKK, thereby inhibiting an already existing biological activity or triggering a new biological activity.

A preferred IKK/NFκB signaling inhibitor in context of the invention is an IKK inhibitor, preferably an IKK$_2$/IKKβ inhibitor. The protein is known as IKK-beta, IKK$_2$, IKKB, NFKBIKB or "inhibitor of nuclear factor kappa B kinase subunit beta" (HumanGene Nomenclature Committee symbol HGNC:5960) and is a protein comprising the amino acid sequence shown in SEQ ID NO: 2 (see https://www.gene-names.org/).

Preferred IKK inhibitors of the invention are selected from SPC839 (Signal Pharmaceutical Inc.), Anilino-Pyrimidine Derivative (Signal Pharmaceutical Inc.), MLN120B or PS1145 (Millennium Pharmaceutical Inc.), BMS-34554 l*(Bristol-Myers Squibb Pharmaceutical Research Institute, IKK inhibitor III), SC-514*(Smithkilne Beecham Corp.), Amino-imidazolecarboxamide derivative (Smithkilne Beecham Corp.), Ureudo-thiophenecarboxamide derivatives (AstraZeneca), Diarylpybidine derivative (Bayer), Pyridooxazinone derivative (Bayer), Indolecarboxamide derivative (Aventis Pharma), Benzoimidazole carboxamide derivative (Aventis Pharma), Pyrazolo[4,3-c]quinoline derivative (Pharmacia Corporation), Imidazolylquinoline-carbxaldehyde semicarbazide derivative (Tulark Inc.), Pyridyl Cyanoguanidine derivate (Leo Pharma), IkB Kinase Inhibitor Peptide (CalBiochem), IKK-2 Inhibitor IV [5-(p-Fluorophenyl)-2-ureido]thiophene-3-carboxamide (CalBiochem), IKK Inhibitor II, Wedelolactone (CalBiochem), IKK Inhibitor VII (CalBiochem), IKK-2 Inhibitor V N-(3,5-Bis-trifluoromethylphenyl)-5-chloro-2-hydroxybenzamide IMD-0354 (CalBiochem) IKK-2 Inhibitor VI (5-Phenyl-2-ureido) thiophene-3-carboxamide (CalBiochem), IKK-2 Inhibitor VIII ACHP 2-Amino-6-(2-(cyclopropylmethoxy)-6-hydroxyphenyl)-4-(4-piperidinyl)-3-pyridinecarbonitrile (CalBiochem), TPCA-1, or BI605906.

In another aspect the problem is solved by an IKK/NFκB signaling inhibitor for use in the prevention or treatment of an inflammatory disease, wherein the prevention or treatment comprises the concomitant or sequential administration of the IKK/NFκB signaling inhibitor and a RIPK$_1$ inhibitor as defined herein. Hence, the present invention provides the combined use of a IKK/NFκB signaling inhibitor, such as an IKK inhibitor, and a RIPK$_1$ inhibitor, in the treatment of subjects suffering from inflammatory diseases. Surprisingly, the combination of the invention could overcome the problem of the prior art of severe side effects caused by IKK/NFκB signaling inhibition, such as the development of neutrophilia and/or the release of IL-1β.

Hence, also provided is a combination (of compounds) for use in the treatment or prevention of an inflammatory disease, wherein the combination comprises an RIPK$_1$ inhibitor and an IKK/NFκB signaling inhibitor as defined herein. Preferably the treatment or prevention comprises the administration of a therapeutically effective amount of an IKK/NFκB signaling inhibitor to a subject suffering from the inflammatory disease. The treatment or prevention also may preferably comprise the administration of a sufficient amount of an RIPK$_1$ inhibitor to the subject to suppress or prevent increased IL-1β release and/or neutrophilia caused by the administration of the IKK/NFκB signaling inhibitor to the subject.

Combinations of the invention, in particular combinations of RIPK$_1$ and IKK inhibitors am preferably provided in a synergistically effective amount. Hence, the combinations of the invention in preferred embodiments is a synergistic combination.

In another aspect, the present invention provides a pharmaceutical composition for use in the treatment or prevention of a disease associated with an increased Interleukin-1β (IL-1β) release in a subject, wherein the pharmaceutical composition comprises a RIPK$_1$ inhibitor as described before together with a pharmaceutically acceptable carrier and/or excipient. Preferably the IL-1β or systemic neutrophilia is a side effect of an IKK inhibitor treatment.

Another aspect pertains to a pharmaceutical composition for use in the treatment or prevention of a disease associated with an increased Interleukin-1β (IL-1β) release or systemic neutrophilia in a subject, wherein the pharmaceutical composition comprises a IKK/NFκB signaling inhibitor as described before together with a pharmaceutically acceptable carrier and/or excipient.

The pharmaceutical composition of the invention is formulated to be compatible with its in-tended route of administration. Examples of routes of administration include parenteral, e.g., intrathecal, intra-arterial, intravenous, intradermal, subcutaneous, oral, transdermal (topical), intracerebroventricular, intraparenchymal, and transmucosal administration. Generally a pharmaceutical composition of the invention shall comprise one or more compounds for inhibiting RIPK$_1$ and/or IKK/NFκB signaling, and at least one pharmaceutically acceptable carrier and/or excipient. The pharmaceutical compositions as described herein are particularly useful for use in the herein described methods for treating immune related diseases.

The term "intrathecal," as used herein, means introduced into or occurring in the space under the arachnoid membrane which covers the brain and spinal cord. The term "intracerebroventricular" refers to administration of a composition into the ventricular system of the brain, e.g., via injection, infusion, or implantation (for example, into a ventricle of the brain). As used herein, the term "intraparenchymal" can refer to an administration directly to brain tissue. In other instances, intraparenchymal administration may be directed to any brain region where delivery of one or more compounds of the invention is effective to mitigate or prevent one or more of disorders as described herein. Forms of administration directly to brain tissue is on some embodiments preferred.

Solutions or suspensions used for parenteral, intradermal, or subcutaneous application can include the following components: a sterile diluent such as water for injection, saline solution, fixed oils, polyethylene glycols, glycerine; propylene glycol or other synthetic solvents; anti-bacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carries include physiological saline, bacteriostatic water, Cremophor EL™ (BASF, Parsippany, N.J.) or phosphate buffered saline (PBS). In all cases, the injectable composition should be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propyleneglycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a sulfotransferase inhibitor) in the required amount in an appropriate solvent with one or a combination of ingredients enumerated above, as required, followed by filtered sterilization Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or cornstarch; a lubricant such as magnesium stearate or Stertes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the pharmaceutical compositions are formulated into ointments, salves, gels, or creams as generally known in the art.

In certain embodiments, the pharmaceutical composition is formulated for sustained or con-trolled release of the active ingredient. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from e.g. Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art.

It is especially advantageous to formulate oral or parenteral compositions in dosage unit form for ease of administration and uniformity of dosage. Dosage unit form as used herein includes physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. The pharmaceutical compositions can be included in a container, pack, or dispenser together with instructions for administration.

The herein disclosed compounds, combinations and compositions are in particular useful in a method of preventing or treating a subject suffering from a disease associated with a pathological or deregulated immune response, such as an increased Interleukin-$\beta$ (IL-1$\beta$) release or systemic neutrophilia, in a cell of the subject, the method comprising the administration of a therapeutically effective amount of a RIPK$_1$ inhibitor to the subject.

In context of the present invention the term "dysregulated immune response" shall refer to any pathological condition characterized by an abnormal, preferably harmful, immune response in a subject. Preferably such an immune response is characterized by an increased release of IL-1$\beta$ or systemic neutrophilia in cells of the immune system, such as a myeloid cell, such as a bone marrow derived myeloid progenitor cell, monocyte or macro-phage. Preferably, such a dysregulated immune response is an adverse effect of a therapy of a subject with an inhibitor of IKK/NF$\kappa$B signaling.

The diseases treatable with the compounds, compositions, combinations and methods of the invention are preferably inflammatory disorders. For purposes of the present invention, the term "inflammatory disease(s)" includes also "autoimmune disease(s)." As used herein, the term "autoimmunity" is generally understood to encompass inflammatory immune-mediated processes involving "self" antigens. In autoimmune diseases, self antigen(s) trigger host immune responses.

Examples of autoimmune and/or inflammatory disorders include, but are not limited to, systemic lupus erythematosus (SLE), discoid lupus, lupus nephritis, sarcoidosis, inflammatory arthritis, including juvenile arthritis, rheumatoid arthritis, psoriatic arthritis, Reiter's syndrome, ankylosing spondylitis, and gouty arthritis, rejection of an organ or tissue transplant, hyperacute, acute, or chronic rejection and/or graft versus host disease, multiple sclerosis, hyper IgE syndrome, polyarteritis nodosa, primary biliary cirrhosis, inflammatory bowel disease, Crohn's disease, ulcerative colitis, celiac's disease (gluten-sensitive enteropathy), autoimmune hepatitis, pernicious anemia, autoimmune hemolytic anemia, psoriasis, scleroderma, myasthenia gravis, autoimmune thrombocytopenic purpura, autoimmune thyroiditis, Grave's disease, Hasimoto's thyroiditis, immune complex disease, chronic fatigue immune dysfunction syndrome (CFIDS), polymyositis and dermatomyositis, cryoglobulinemia, thrombolysis, cardiomyopathy, pemphigus vulgaris, pulmonary interstitial fibrosis, Type I and Type II diabetes mellitus, type 1, 2, 3, and 4 delayed-type hypersensitivity, allergy or allergic disorders, unwanted/unintended immune responses to therapeutic proteins (see for example Koren, et al. (2002) Curr. Pharm. Biotechnol. 3:349-60), asthma, Churg-Strauss syndrome (allergic granulomatosis), atopic dermatitis, allergic and irritant contact dermatitis, urtecaria, IgE-mediated allergy, atherosclerosis, vasculitis, idiopathic inflammatory myopathies, hemolytic disease, Alzheimer's disease, Amyotrophic Lateral Sclerosis (AIS), chronic inflammatory demyelinating polyneuropathy, and the like.

Cells associated with the diseases to be treated according to the invention are preferably a myeloid cell, such as a bone marrow derived myeloid progenitor cell, monocyte or macrophage.

In another aspect of the invention there is provided a method for the treatment of an inflammatory disease in a subject, the method comprising the concomitant or sequential administration to the subject of a therapeutically effective amount of (i) a RIPK$_1$ inhibitor and (ii) a IKK/NF$\kappa$B signaling inhibitor.

As mentioned earlier, a preferred embodiment of the invention pertains to a use of the herein disclosed compounds, combinations, compositions and methods for the treatment of adverse effects induced by a therapy with a IKK/NF$\kappa$B signaling inhibitors. As an explanation, the embodiment relates to a medical use where a subject suffers from a disorder that is primarily treated using an IKK/NF$\kappa$B signaling inhibitor. However, such therapies often a reassociated with severe adverse effects. The present invention therefore in some embodiments provides a preventive/therapeutic treatment of such side effects by administering to the same subject RIPK$_1$ inhibitor in accordance with the herein provided disclosure. Hence, in some further embodiment, the disease to be treated is a side effect or adverse event associated with RIPK$_1$ activity. In alternative or additional embodiments the primary disorder (meaning herein the disorder treated by the use of a IKK/NF$\kappa$B signaling inhibitors) is a disorder that is not associated with RIPK$_1$.

In some embodiments the terms "adverse effect", "adverse event", or "side effect" shall mean a medical unfavorable condition induced, caused or worsened by treating a patient suffering from a given disease (here primary disease) with a therapy/therapeutic indicated for that given (primary) disease. Therefore, in context of the herein disclosed invention it may be preferred that a side effect or adverse effect occurring in a subject as a secondary disease, wherein the subject suffers from a primary disease different from the secondary disease, is treated by the herein disclosed compounds, compositions, combinations and/methods, most preferably the herein disclosed RIPK$_1$ inhibitors.

Figure 1B:
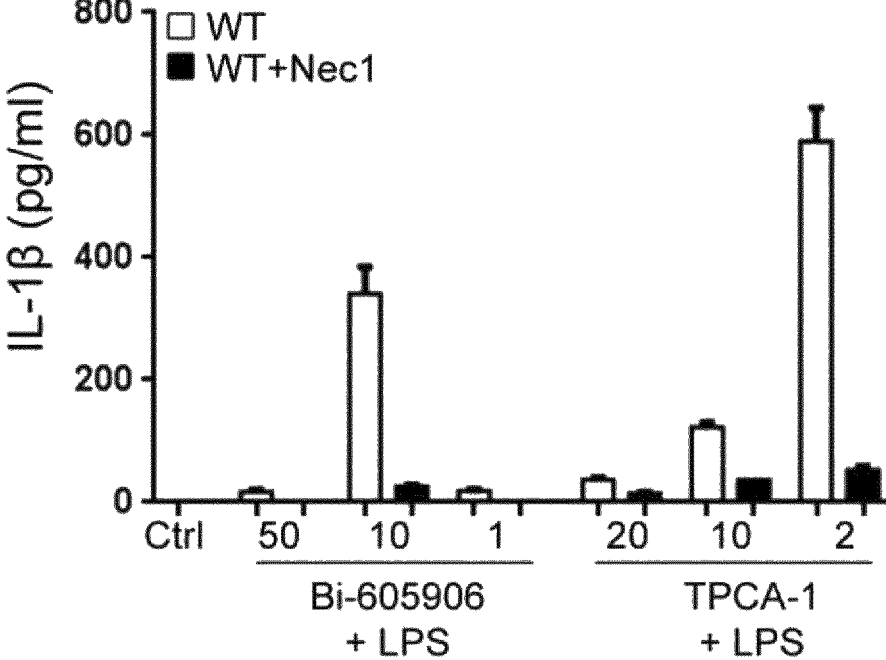

The present invention will now be further described in the following examples with reference to the accompanying figures and sequences, nevertheless, without being limited thereto. For the purposes of the present invention, all references as cited herein are incorporated by reference in their entireties. In the Figures:

FIG. 1: Genetic (A) or pharmacologic (B) inactivation of the kinase activity of RIPK$_1$ abrogates LPS-induced IL-1$\beta$ secretion in BMDMs treated with different concentrations of IKK$_2$ inhibitors. Each bar represents the mean+/−SEM values of triplicate samples for each condition.

FIG. 2: Generation of knock-in mice expressing kinase inactive IKK$_2$ from the endogenous Ikk$_2$ genomic locus by mutating lysine 44 to alanine (K44A) using CRISPR/Cas9-mediated gene targeting. a) Schematic depiction of the murine Ikk$_2$ genomic locus indicating the location of lysine 44 on exon 3 (upper panel), as well as the sequence of the wild type exon 3 and the mutated exon 3 indicating the designed mutation changing lysine 44 to alanine (AAG to GCG) (lower panel). b) Tables depicting the number of litters and the total number as well as the number of $Ikk_2^{K44A/K44A}$ mice obtained from the indicated breedings. Note that $Ikk_2^{K44A/K44A}$ mice were only obtained in the $Ripk1^{D138N/D138N}$ genetic background. c) DNA sequencing of genomic DNA from wild type and homozygous $Ikk_2^{K44A/K44A}$ mice shows that the planned mutation was correctly introduced in exon 3.

Figure 3:
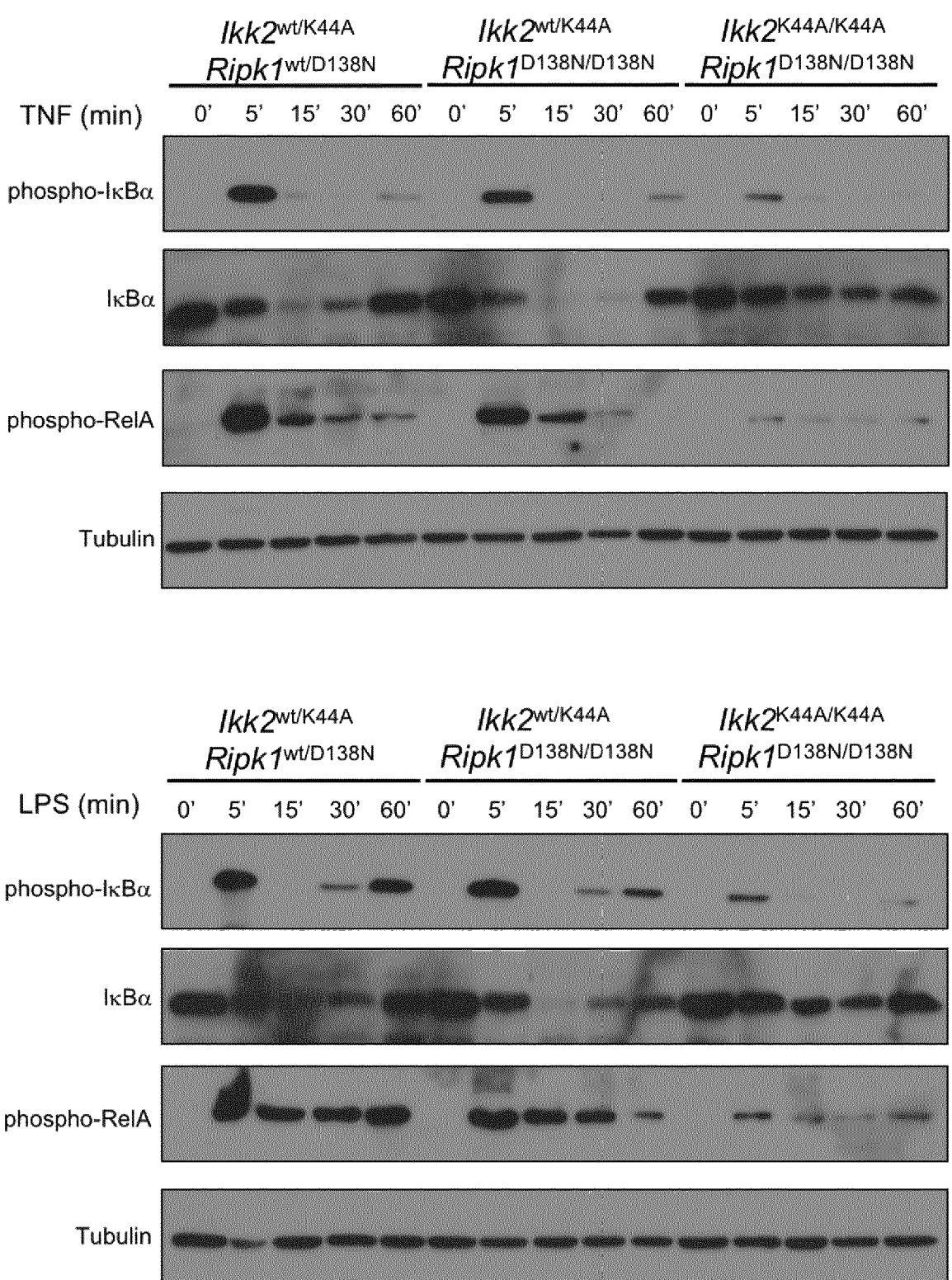

FIG. 3: Loss of $IKK_2$ kinase activity in cells expressing mutated $IKK_2$ K44A strongly suppresses NF-κB activation in response to TNF and LPS in bone marrow derived macrophages (BMDMs). Bone marrow was isolated from femur and tibia of 2-week-old control ($IKK_2^{wt/K44A}$; $Ripk1^{wt/D138N}$ and $IKK_2^{wt/K44A}$;$Ripk1^{D138N/D138N}$) and $IKK_2$ kinase inactive $IKK_2^{K44A/K44A}$;$Ripk1^{D138N/D138N}$) mice. BMDMs were differentiated in the presence of 20 ng/ml M-CSF (Thermo Fisher Scientific, #14-8983-62) for 7 days and seeded at $1\times10^6$ cells in 6-well cell culture dishes. On day 8, time course-stimulations with TNF (20 ng/ml) and LPS (100 ng/ml) were performed in the presence of M-CSF (20 ng/ml), and cell-lysates were prepared on ice using RIPA buffer supplemented with protease and phosphatase inhibitors. Proteins (20 μg) were separated by SDS-PAGE and Western Blots were performed using the following antibodies: phospho-IκBα S32/36 (Cell Signaling, #9246L) IκBα (Santa Cruz Biotechnologies, #K1315), phospho-RelAS536 (Cell Signaling, #3036S), and Alpha Tubulin (Sigma-Aldrich, #T6074). Note strongly suppressed phosphorylation and degradation of IκBα as well as phosphorylation of RelA in cells homozygously expressing kinase inactive $IKK_2$, compared to the control cells that carry one wild type and one kinase inactive $IKK_2$ allele. The $RIPK_1$D138N mutation does not affect NF-κB activation (Polykratis et al, 2014, J Immunol 193: 1539-1543).

Figure 4:
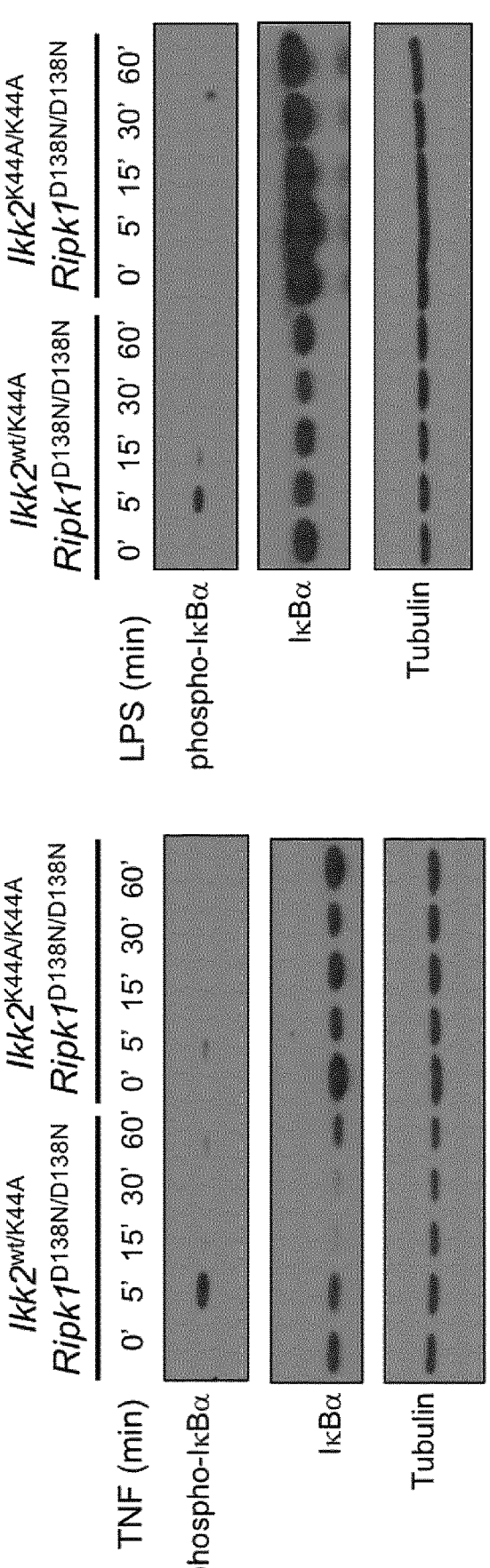

FIG. 4: Loss of $IKK_2$ kinase activity in cells expressing mutated $IKK_2$ K44A strongly suppresses NF-κB activation in response to TNF and LPS in lung fibroblasts. Lung fibroblasts were isolated from two-week old control ($IKK_2^{wt/K44A}$; $Ripk1^{D138N/D138N}$), and $IKK_2$ and Ripk1 kinase dead ($IKK_2^{wt/K44A}$; $Ripk1^{D138N/D138N}$) mice. Lungs were disrupted using scissors and collagenase treatment, and subsequently cultured for 7 days. On day 7, lung fibroblasts were seeded at $1\times10^6$ cells in 6-well cell culture dishes. On day 8, Time course-stimulations with TNF (20 ng/ml) and LPS (100 ng/ml) were performed, and cell-lysates were prepared on ice using RIPA buffer supplemented with protease and phosphatase inhibitors. Proteins (20 μg) were separated by SDS-PAGE and Western Blots were performed using the following antibodies: phospho-IκBα S32/36 (Cell Signaling, #9246L), IκBα (Santa Cruz Biotechnologies, #K1315) and Alpha Tubulin (Sigma-Aldrich, #T6074).

Figure 5:
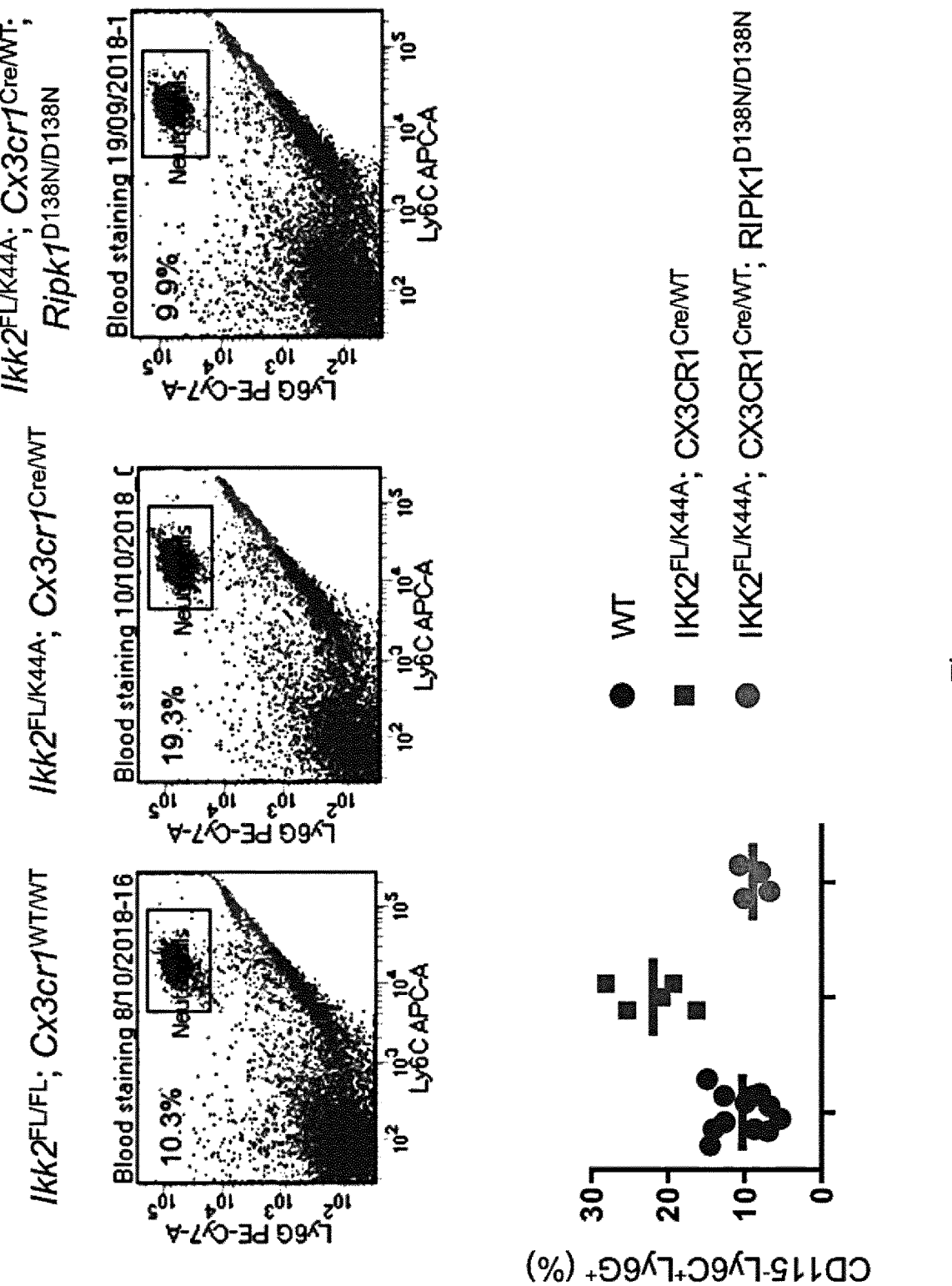

FIG. 5: Inhibition of $RIPK_1$ kinase activity prevents the development of neutrophilia in mice with myeloid cell specific inhibition of $IKK_2$ kinase activity. The presence of neutrophils was assessed by flow cytometry on peripheral blood collected from 2.5 month old control mice ($Ikk_2^{FL/FL}$, $Cx3cr1^{WT/WT}$), mice with macrophage specific inhibition of $IKK_2$ kinase activity ($Ikk_2^{FL/K44A}$; $Cx3cr1^{Cre/WT}$) and mice with macrophage specific inhibition of $IKK_2$ kinase activity that also lack $RIPK_1$ kinase activity in all cells ($Ikk_2^{FL/K44A}$; $Cx3cr1^{Cre/WT}$;$Ripk1^{D138N/D138N}$). Neutrophils were determined as CD115 Ly6G+Ly6C+ leukocytes. Whole blood (50 μL) was stained using the following antibodies at indicated dilutions: CD115 (Biolegend, #135512) $\frac{1}{100}$, Ly6G (Biolegend, #127618) $\frac{1}{200}$, Ly6C (Biolegend, #128016) $\frac{1}{200}$, Life/

Dead (Life technologies, #L34959) $\frac{1}{400}$. Red blood celllysis and fixation was done using Fix/Lyse solution (eBioscience, #00-5333-54). Stained cells were resus-pended in PBS supplemented with 0.5% FCS and acquisition was performed using an LSR Fortessa (BD Biosciences). Representative FACS plots are shown from mice with the indicated genotypes. The graph shows the percentage of CD115Ly6G+ Ly6C+ leukocytes in mice with the indicated genotypes. Each dot represents an individual mouse. Note that lack of $RIPK_1$ kinase activity fully prevents the neutrophilia caused by inhibition of $IKK_2$ kinase activity.

(RIPK1 isoform 1)

SEQ ID NO: 1

MQPDMSLNVIKMKSSDFLESAELDSGGFGKVSLCFHRTQGLMIMKTVYKG

PNCIEHNEALLEEAKMMNRLRHSRVVKLLGVIIEEGKYSLVMEYMEKGNL

MHVLKAEMSTPLSVKGRIILEIIEGMCYLHGKGVIHKDLKPENILVDNDF

HIKIADLGLASFKMWSKLNNEEHNELREVDGTAKKNGGTLYYMAPEHLND

VNAKPTEKSDVYSFAVVLWAIFANKEPYENAICEQQLIMCIKSGNRPDVD

DITEYCPREIISLMKLCWEANPEARPTFPGIEEKFRPFYLSQLEESVEED

VKSLKKEYSNENAVVKRMQSLQLDCVAVPSSRSNSATEQPGSLHSSQGLG

MGPVEESWFAPSLEHPQEENEPSLQSKLQDEANYHLYGSRMDRQTKQQPR

QNVAYNREEERRRRVSHDPFAQQRPYENFQNTEGKGTAYSSAASHGNAVH

QPSGLTSQPQVLYQNNGLYSSHGFGTRPLDPGTAGPRVWYRPIPSHMPSL

HNIPVPETNYLGNTPTMPFSSLPPTDESIKYTIYNSTGIQIGAYNYMEIG

GTSSSLLDSTNTNFKEEPAAKYQAIFDNTTSLTDKHLDPIRENLGKHVVK

NCARKLGFTQSQIDEIDHDYERDGLKEKVYQMLQKWVMREGIKGATVGKL

AQALHQCSRIDLLSSLIYVSQN (IKK2 isoform 1)

SEQ ID NO: 2

MSWSPSLTTQTCGAWEMKERLGTGGFGNVIRWHNQETGEQIAIKQCRQEL

SPRNRERWCLEIQIMRRLTHPNVVAARDVPEGMQNLAPNDLPLLAMEYCQ

GGDLRKYLNQFENCCGLREGAILTLLSDIASALRYLHENRIIHRDLKPEN

IVLQQGEQRLIHKIIDLGYAKELDQGSLCTSFVGTLQYLAPELLEQQKYT

VTVDYWSFGTLAFECITGFRPFLPNWQPVQWHSKVRQKSEVDIVVSEDLN

GTVKFSSSLPYPNNLNSVLAERLEKWLQLMLMWHPRQRGTDPTYGPNGCF

KALDDILNLKLVHILNMVTGTIHTYPVTEDESLQSLKARIQQDTGIPEED

QELLQEAGLALIPDKPATQCISDGKLNEGHTLDMDLVFLFDNSKITYETQ

ISPRPQPESVSCILQEPKRNLAFFQLRKVWGQVVVHSIQTLKEDCNRLQQ

GQRAAMMNLLRNNSCLSKMKNSMASMSQQLKAKLDFFKTSIQIDLEKYSE

QTEFGITSDKLLLAWREMEQAVELCGRENEVKLLVERMMALQTDIVDLQR

SPMGRKQGGTLDDLEEQARELYRRLREKPRDQRTEGDSQEMVRLLLQAIQ

SFEKKVRVIYTQLSKTVVCKQKALELLPKVEEVVSLMNEDEKTVVRLQEK

-continued

RQKELWNLLKIACSKVRGPVSGSPDSMNASRLSQPGQLMSQPSTASNSLP

EPAKKSEELVAEAHNLCTLLENAIQDTVREQDQSFTALDWSWLQTEEEEH

SCLEQAS

SEQ ID NO: 3 to 7 Depict Sequences Disclosed in FIG. 2.

EXAMPLES

Example 1: Inhibition of RIPK₁ Kinase Activity Prevents LPS-Induced IL-1β Production in Macrophages Treated with Pharmacological IKK Inhibitors Experimental Procedures:

Bone marrow was isolated from the tibiae and femurs of one WT and one Ripk1$^{D138N/D138N}$ mouse (6-7 week old). Bone marrow from one leg of each mouse was immediately frozen Bone marrow cells from the other leg were spun down at 1200 rpm, for 5 min and seeded in 15 cm² non-treated cell culture plates in 20 ml of medium containing 10 ng/ml M-CSF. Cells were allowed to differentiate for six days and subsequently adherent BMDMs were lifted, counted and seeded at a density of 2×10⁵ cells/well in a 48 well plate. The day after, cells were pretreated with different concentrations of the IKK₂ inhibitors for 30 min before stimulation with 100 ng/ml LPS in a total volume of 250 µl. Each experimental condition was assayed in triplicate. 20-24 h later supernatants were removed, cleared from floating cells and were frozen until cytokine measurements. IL-1β concentration was determined with a specific ELISA (eBioscience) following the manufacturer's instructions.

For the experiment with Nec1 the frozen bone marrow cells were used. After thawing, macrophages were differentiated as described above for fresh bone marrow cells. Necrostatin-1 (Nec-1) was added together with the IKK₂ inhibitors during the 30 min pretreatment BMDMs were stimulated with LPS for 20-24 h and supernatants were kept for ELISA measurements.

Results:

Treatment of wild type (WT) bone marrow derived macrophages (BMDMs) with two different inhibitors of IKK₂/IKKβ resulted in IL-1β secretion upon LPS Stimulation. Both IKK₂ Inhibitors used potentiated IL-1β secretion albeit to different extent, with TPCA-1 exhibiting greater potency. Genetic, using BMDMs from knock-in mice expressing a kinase inactive RIPK₁$^{D138N}$ mutant, (FIG. 1A) or pharmacological, using Necrostatin-1, (FIG. 1B) inhibition of the kinase activity of RIPK₁ strongly reduced the amount of secreted IL-1β, showing that upon IKK₂ inhibition LPS-induced IL-1β secretion in BMDMs depends on RIPK₁ kinase activity.

Reagents:

Medium: DMEM, 10% FCS, 2 mM glutamine, 1 mM Sodium Pyruvate, 10 mM HEPES,

100 U/ml Penicillin, 100 pg/ml Streptomycin

M-CSF: 10 ng/ml (Immunotools)

Nec1: 30 pM (Enzo)

LPS: 100 ng/ml (*Salmonella enterica* serotype *enteritidis*, Sigma)

Bi-605906 (Hycultec)

TPCA-1 (Tocris)

Figure 2A:
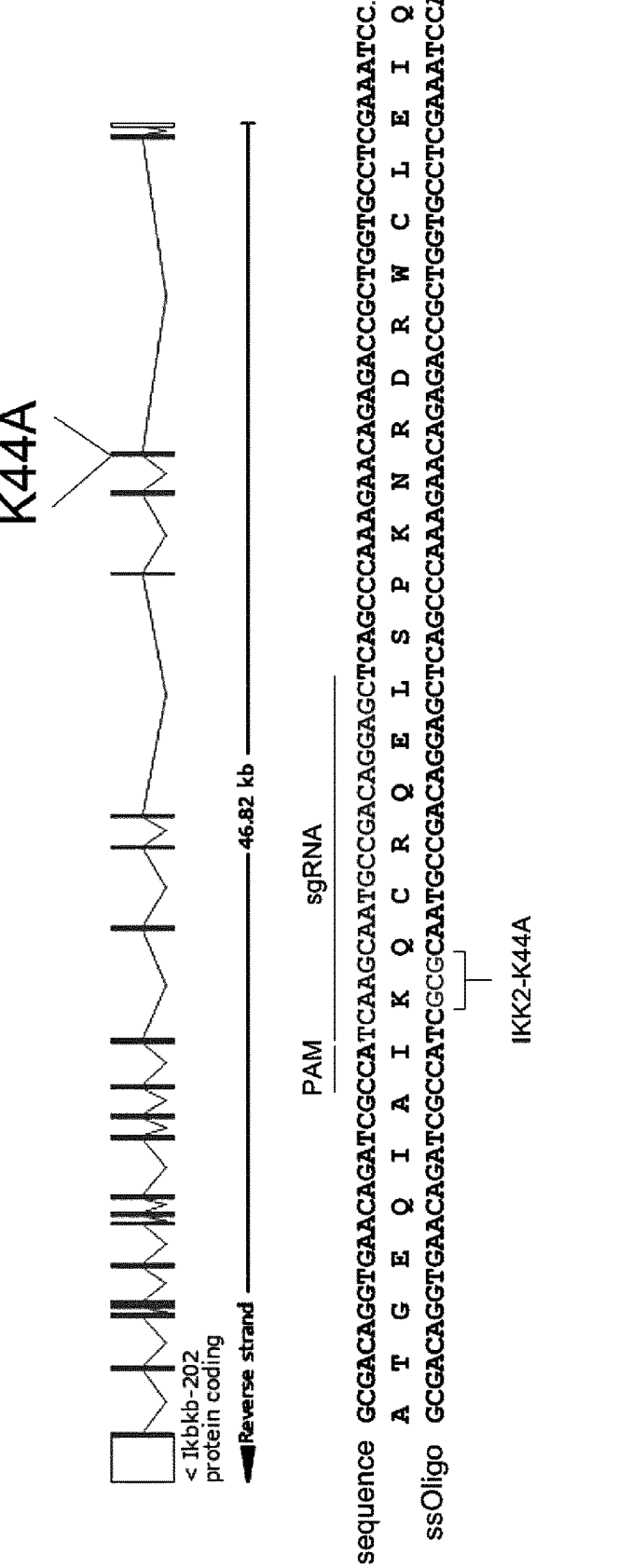
Figure 2C:
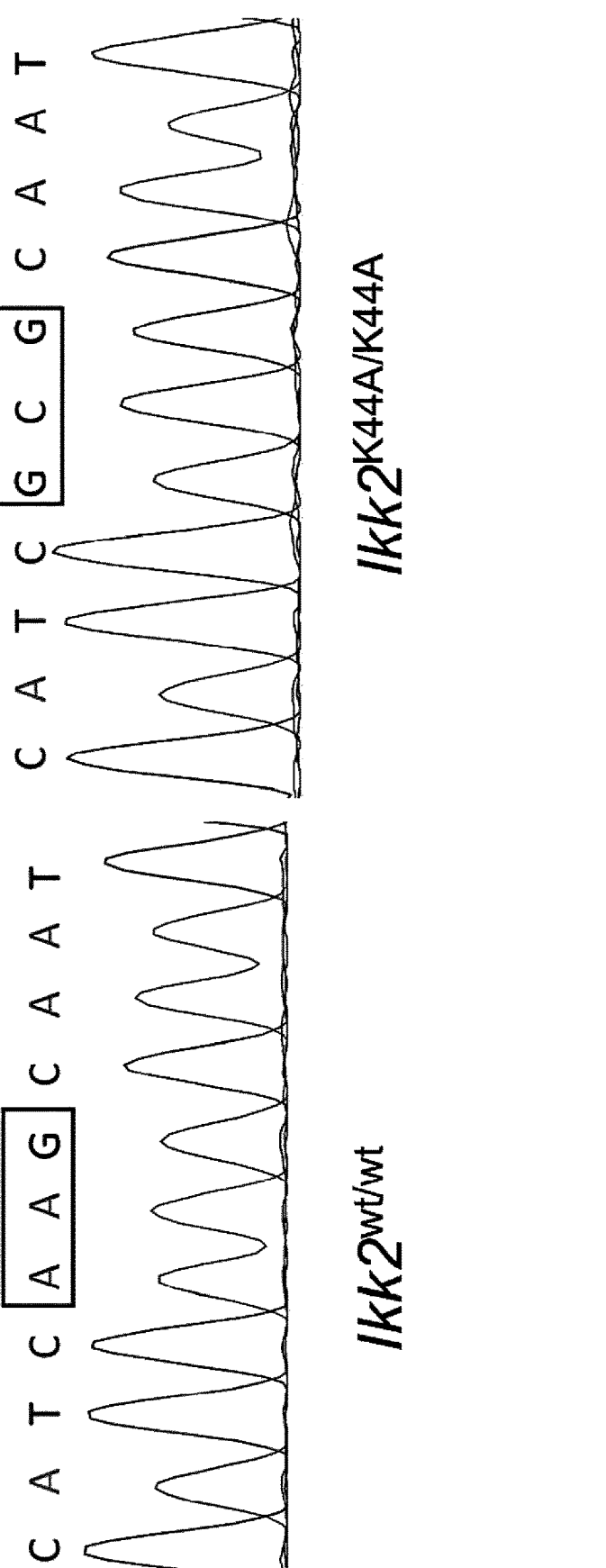

Example 2: Inhibition of RIPK₁ Kinase Activity Prevents the Development of Systemic Neutrophilia Caused by Inhibition of IKK₂ Kinase Activity in Macrophages To address the role IKK₂ kinase activity in vivo we generated knock-in mice expressing kinase inactive IKK₂ from the endogenous Ikk₂ genomic locus. Specifically, we used CRISPR/Cas9-mediated targeted mutagenesis to introduce a two nucleotide change in exon 3 of the ikk2 gene, which changes the codon encoding for lysine 44 (AAG) to a codon encoding alanine (GCG) (FIG. 2a). Mutation of lysine 44 in the ATP binding pocket of IKK₂ inactivates its catalytic activity (E Zandi et al., Cell 91, no. 2 (Oct. 17, 1997): 243-52.). sgRNA targeting the Ikk₂ gene together with the repair oligo containing the desired mutation as well as Cas9 were microinjected into the pronucleus of zygotes from C57B1/6 mice, resulting in the generation of founder mice that transmitted the K44A mutation to their progeny. Heterozygous Ikk₂$^{K44A/wt}$ mice were viable, developed to adulthood, were fertile and did not show any abnormalities. Heterozygous breedings of Ikk₂$^{K44A/wt}$ mice failed to produce viable homozygous Ikk₂$^{K44A/K44A}$ offspring, consistent with the embryonic lethality observed in mice lacking IKK₂ (Q Li et al., Science (New York, NY) 284, no. 5412 (Apr. 9, 1999): 321-25). To address whether the embryonic lethality of Ikk₂$^{K44A/K44A}$ mice depends on RIPK₁ kinase activity the inventors bred these mice with Ripk1$^{D138N/D138N}$ knock-in animals expressing kinase inactive RIPK₁. Indeed, the inventors obtained viable Ikk₂$^{K44A/K44A}$ Ripk1$^{D138N/D138N}$ mice showing that inhibition of RIPK₁ kinase activity rescues the embryonic lethality of Ikk₂$^{K44A/K44A}$ mice (FIG. 2b). Sequencing of the Ikk₂ gene from Ikk₂$^{K44A/K44A}$ Ripk1$^{D138N/D138N}$ mice confirmed the correct mutation AAG to GCG that changes lysine 44 to alanine (FIG. 2c). Although the double kinase inactive Ikk₂$^{K44A/K44A}$ Ripk1$^{D138N/D138N}$ mice were born normally, they showed reduced growth and needed to be sacrificed at the age of 2 weeks, likely due to infection with opportunistic bacteria as shown before in double RelA and TNFR1 knockout animals that were also born but died during the first 3 weeks afterbirth due to bacterial infections (E Alcamo et al., Journal of Immunology (Baltimore, Md: 1950) 167, no. 3 (Aug. 1, 2001): 1592-1600.). These results showed that RIPK₁ kinase activity mediates the embryonic lethal phenotype of Ikk₂$^{K44A/K44A}$ mice but mice lacking the kinase activities of both IKK₂ and RIPK₁ die after birth likely due to severe immune deficiency.

To confirm that the K44A mutation abolished the kinase activity of IKK₂ the inventors ana-lysed the activation of NF-κB in bone marrow derived macrophages (BMDMs) from Ikk₂$^{K44A/K44A}$ Ripk1$^{D138N/D138N}$ mice as well as control cells. As shown in FIG. 3, BMDMs from Ikk₂$^{K44A/K44A}$ Ripk1$^{D138N/D138N}$ mice showed very strongly suppressed activation of NF-κB, as indicated by impaired phosphorylation and degradation of IκBα as well as phosphorylation of RelA/p65 in response to stimulation by TNF or LPS. Similar results were obtained by measuring activation of NF-κB in lung fibroblasts from Ikk₂$^{K44A/K44A}$ Ripk1$^{D138N/D138N}$ and control mice in response to TNF or LPS (FIG. 4). These results confirmed that the K44A mutation abolished the kinase activity of IKK$_2$ and very strongly suppresses the activation of NF-κB by TNF or LPS.

Myeloid cell specific knockout of IKK$_2$ as well as treatment of the mice with IKK$_2$ kinase inhibitors resulted in the development of systemic neutrophilia (Greten et al, DOI: 10.1016/j.cell.2007.07.009, Hsu et al, DOI: 10.1038/ni.1976). These findings raised serious concerns about the safety of IKK/NF-κB signaling inhibitors, which made several companies terminate their programs for the development and therapeutic application of IKK inhibitors. The inventors hypothesized that the development of neutrophilia in response to IKK$_2$ inhibition could be caused by RIPK$_1$ kinase activity and aimed to address this hypothesis using genetic experiments. The inventors generated mice with inhibition of IKK$_2$ kinase activity in myeloid cells, by crossing mice carrying one K44A and one loxP-flanked IKK$_2$ allele (Ikk$_2$$^{FL/K44A}$) with Cx3cr1-Cre mice expressing Cre recombinase specifically in macrophages (Simon Yona et al., "Fate Mapping Reveals Origins and Dynamics of Monocytes and Tissue Macrophages Under Homeostasis.," Immunity 38, no. 1 (Jan. 24, 2013): 79-91, doi:10.116/j.immuni.2012.12.001). In these animals, Cre recombinase deletes the loxP-flanked IKK$_2$ allele that expresses wild type IKK$_2$ resulting in expression exclusively of the kinase inactive IKK$_2$K44A in macrophages. Consistent with the earlier studies based on myeloid cell specific knockout of IKK$_2$ as well as treatment of mice with IKK$_2$ kinase inhibitors, the inventors found that inhibition of IKK$_2$ kinase activity in macrophages resulted in the development of systemic neutrophilia in mice, as shown by the analysis of neutrophils in the blood (FIG. 5). Importantly, crossing the Ikk$_2$$^{FL/K44A}$; Cx3cr1-Cre mice with Ripk1$^{D138N/D138N}$ animals rescued the development of neutrophilia, as shown by the normal amount of neutrophils in the blood of Ikk$_2$$^{FL/K44A}$;Cx3cr1-Cre; Ripk1$^{D138N/D138N}$ mice (FIG. 4). These findings provide experimental proof that the development of systemic neutrophilia by inhibition of IKK$_2$ kinase activity is dependent on RIPK$_1$ kinase activity.

Based on these findings, the inventors propose that administration of RIPK$_1$ kinase inhibitors will overcome the serious adverse effects of inhibitors of IKK/NF-κB, thereby allowing the safe application of drugs inhibiting IKK/NF-κB signaling for the treatment of inflammatory diseases. Since inhibition of RIPK$_1$ kinase activity has also been reported to inhibit inflammation in some models of acute and chronic inflammatory pathologies, co-administration of RIPK$_1$ inhibitors with IKK/NF-κB inhibitors may not only prevent the adverse side effects of the latter but may also have a synergistic effect by combining the therapeutic effects of the two inhibitors.

---

The invention claimed is:

1. A method of treating a deregulated immune response in a subject, wherein the deregulated immune response is systemic neutrophilia or increased interleukin-1β (IL-1β) caused as a side effect by inhibiting inhibitor of κB (IκB) kinase (IKK)/nuclear factor κB (NFκB) signaling in a cell of the subject, wherein the method comprises:

inhibiting a receptor-interacting serine/threonine-protein kinase 1 (RIPK1) in the cell of the subject, wherein the inhibition of IKK/NFκB signaling comprises administering SPC839, MLN120B, PS1145, SC-514*, IκB kinase inhibitor peptide, [5-(p-fluorophenyl)-2-ureido]thiophene-3-carboxamide (TPCA-1), wedelolactone, N-(3,5-bistrifluoromethylphenyl)-5-chloro-2-hydroxybenzamide (IMD-0354), (5-phenyl-2-ureido)thiophene-3-carboxamide (IKK-2 inhibitor VI), 2-amino-6-(2-(cyclopropylmethoxy)-6-hydroxyphenyl)-4-(4-piperidinyl)-3-pyridinecarbonitrile (ACHP), or B1605906 to the subject, and wherein the inhibition of the RIPK1 comprises administering GSK2982772, necrostatin-1, or necrostatin-1 stable to the subject.

2. The method of claim 1, wherein the side effect is increased interleukin-1β (IL-1β) release.

3. The method of claim 2, wherein the subject is suffering from an inflammatory disease.

4. The method of claim 1, wherein the method comprises the concomitant inhibition of the $RIPK_1$ and inhibition of IKK/NFκB signaling in the cell of the subject.

5. The method of claim 2, wherein the side effect is caused by inhibiting an IKK in the cell of the subject.

6. The method of claim 5, wherein the side effect is caused by inhibiting an $IKK_2/IKK\beta$ in the cell of the subject.

7. The method of claim 1, wherein the method comprises inhibiting IKK/NFκB signaling in the cell of the subject and then inhibiting the $RIPK_1$ in the cell of the subject.

8. The method of claim 1, wherein the method comprises inhibiting the RIPK1 in the cell of the subject and then inhibiting IKK/NFκB signaling in the cell of the subject.

9. The method of claim 1, wherein the systemic neutrophilia is caused by the inhibition of IKK/NFκB signaling in macrophages of the subject.

10. The method of claim 1, wherein the kinase activity of the RIPK1 and the IKK/NFκB signaling in a macrophage in the subject are inhibited, thereby suppressing IKK/NFκB signaling dependent IL-1β production in the macrophage.

11. A method of inhibiting the development of neutrophilia in a subject, wherein the neutrophilia is caused by the inhibition of IKK/NFκB signaling in macrophages of the subject, wherein the method comprises a step of inhibiting RIPK1 in cells of the subject, wherein the inhibition of IKK/NFκB signaling comprises administering SPC839, MLN120B, PS1145, SC-514*, IκB kinase inhibitor peptide, [5-(p-fluorophenyl)-2-ureido]thiophene-3-carboxamide (TPCA-1), wedelolactone, N-(3,5-bistrifluoromethylphenyl)-5-chloro-2-hydroxybenzamide (IMD-0354), (5-phenyl-2-ureido) thiophene-3-carboxamide (IKK-2 inhibitor VI), 2-amino-6-(2-(cyclopropylmethoxy)-6-hydroxyphenyl)-4-(4-piperidinyl)-3-pyridinecarbonitrile (ACHP), or B1605906 to the subject, and wherein the inhibition of the RIPK1 comprises administering GSK2982772, necrostatin-1, or necrostatin-1 stable to the subject.

12. A method of suppressing IL-1β production induced by inhibition of IKK/NFκB signaling in a macrophage, the method comprising inhibiting in the macrophage RIPK1 and IKK/NFκB signaling simultaneously, wherein the inhibition of IKK/NFκB signaling comprises administering SPC839, MLN120B, PS1145, SC-514*, IκB kinase inhibitor peptide, [5-(p-fluorophenyl)-2-ureido]thiophene-3-carboxamide (TPCA-1), wedelolactone, N-(3,5-bistrifluoromethylphenyl)-5-chloro-2-hydroxybenzamide (IMD-0354), (5-phenyl-2-ureido) thiophene-3-carboxamide (IKK-2 inhibitor VI), 2-amino-6-(2-(cyclopropylmethoxy)-6-hydroxyphenyl)-4-(4-piperidinyl)-3-pyridinecarbonitrile (ACHP), or B1605906 to the subject, and wherein the inhibition of the RIPK1 comprises administering GSK2982772, necrostatin-1, or necrostatin-1 stable to the subject.

13. A method of treating a deregulated immune response in a subject, wherein the deregulated immune response is increased interleukin-10 (IL-1β) caused as a side effect by inhibiting inhibitor of κB (IκB) kinase (IKK)/nuclear factor κB (NFκB) signaling in a cell of the subject, wherein the method comprises:

inhibiting a receptor-interacting serine/threonine-protein kinase 1 (RIPK1) in the cell of the subject, wherein the inhibition of IKK/NFκB signaling comprises administering SPC839, MLN120B, PS1145, SC-514*, IκB kinase inhibitor peptide, [5-(p-fluorphenyl)-2-ureido]thiophene-3-carboxamide (TPCA-1), wedelolactone, N-(3,5-bistrifluoromethylphenyl)-5-chloro-2-hydroxybenzamide (IMD-0354), (5-phenyl-2-ureido) thiophene-3-carboxamide (IKK-2 inhibitor VI), 2-amino-6-(2-(cyclopropylmethoxy)-6-hydroxyphenyl)-4-(4-piperidinyl)-3-pyridinecarbonitrile (ACHP), or B1605906 to the subject, and wherein the inhibition of the RIPK1 comprises administering GSK2982772, necrostatin-1, or necrostatin-1 stable to the subject.

\* \* \* \* \*